United States Patent [19]

Dettbarn et al.

[11] 4,400,172
[45] Aug. 23, 1983

[54] NEEDLE-LESS INJECTION INSTRUMENT

[75] Inventors: Hans-Jürgen Dettbarn, Marburg/Lahn; Josef Zimmermann, Sulzbach, both of Fed. Rep. of Germany

[73] Assignee: Hoechst Aktiengesellschaft, Frankfurt am Main, Fed. Rep. of Germany

[21] Appl. No.: 368,169

[22] Filed: Apr. 14, 1982

[30] Foreign Application Priority Data

Apr. 16, 1981 [DE] Fed. Rep. of Germany ....... 3115373

[51] Int. Cl.³ .............................................. A61M 5/30
[52] U.S. Cl. ......................................................604/70
[58] Field of Search ...................... 604/68, 48, 70, 71, 604/73, 140, 141, 149, 150, 131, 181

[56] References Cited

U.S. PATENT DOCUMENTS

| 2,928,390 | 3/1960 | Venditty et al. | 604/70 |
| 3,330,276 | 7/1967 | Gordon | 604/71 |
| 3,561,443 | 2/1971 | Banker | 604/70 |
| 4,103,684 | 8/1978 | Ismach | 604/71 |

Primary Examiner—John D. Yasko
Attorney, Agent, or Firm—Curtis, Morris & Safford

[57] ABSTRACT

In this injection instrument, the piston pump (A) is connected releasably to a drive motor (B), the working piston (5) of which is arranged displaceably in a cylindrical bore (6) of the motor housing (1).

So that the piston pump (A) can be coupled to and uncoupled from the drive motor (B) by simple manipulations under sterile conditions and so that a ram play independent of the particular piston stroke is present between the piston pump and drive motor, the pump housing (20) has on the pump head (17) an annular groove (18) and a pair of flattened portions (22, 23) which are parallel to one another and reach to the bottom of the annular groove (18). The pump plunger (2) on the peg (8) projecting from the pump chamber (7) of the pump housing (20) is provided with two equally deep annular grooves (9, 10) located next to one another and with two pairs of flattened portions (11, 12, 13, 14) which are each parallel to one another and which reach to the bottom of the annular grooves (9, 10), one pair of flattened portions (11, 12 or 13, 14) extending only from the annular groove (9) to the annular groove (10) and being arranged perpendicularly to the second pair of flattened portions. Two pins (15, 16, 27, 28) are arranged, parallel to one another, respectively in the motor housing (1) and in a bore (19) in the piston shaft (4) and engage into the annular groove (18) of the pump housing (20) and the annular grooves (9) and (10) of the pump plunger (2). The pump plunger (2) and the piston shaft (4) are provided with devices preventing them from rotating in their housings.

2 Claims, 9 Drawing Figures

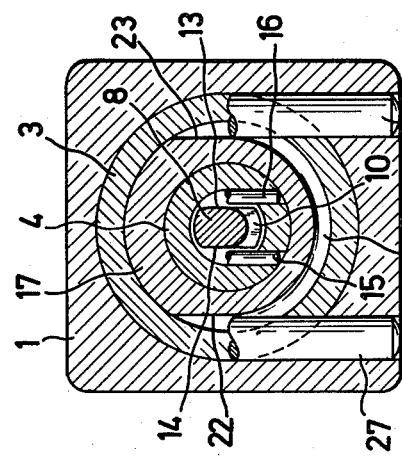
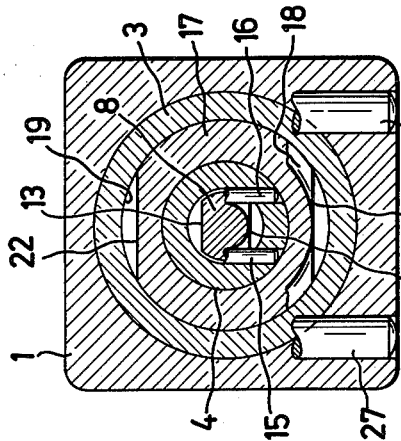
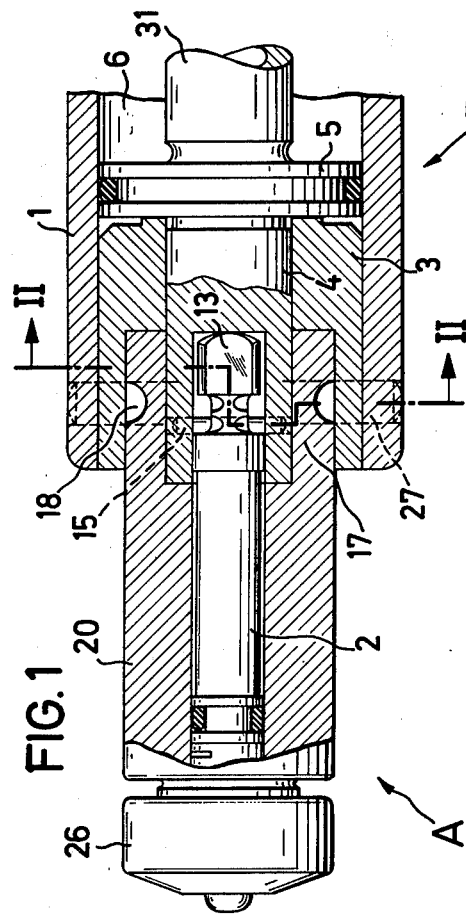
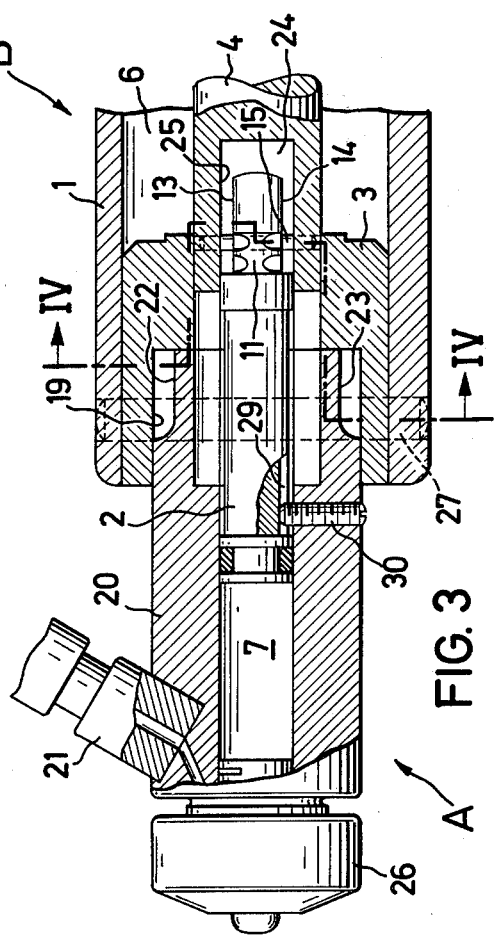

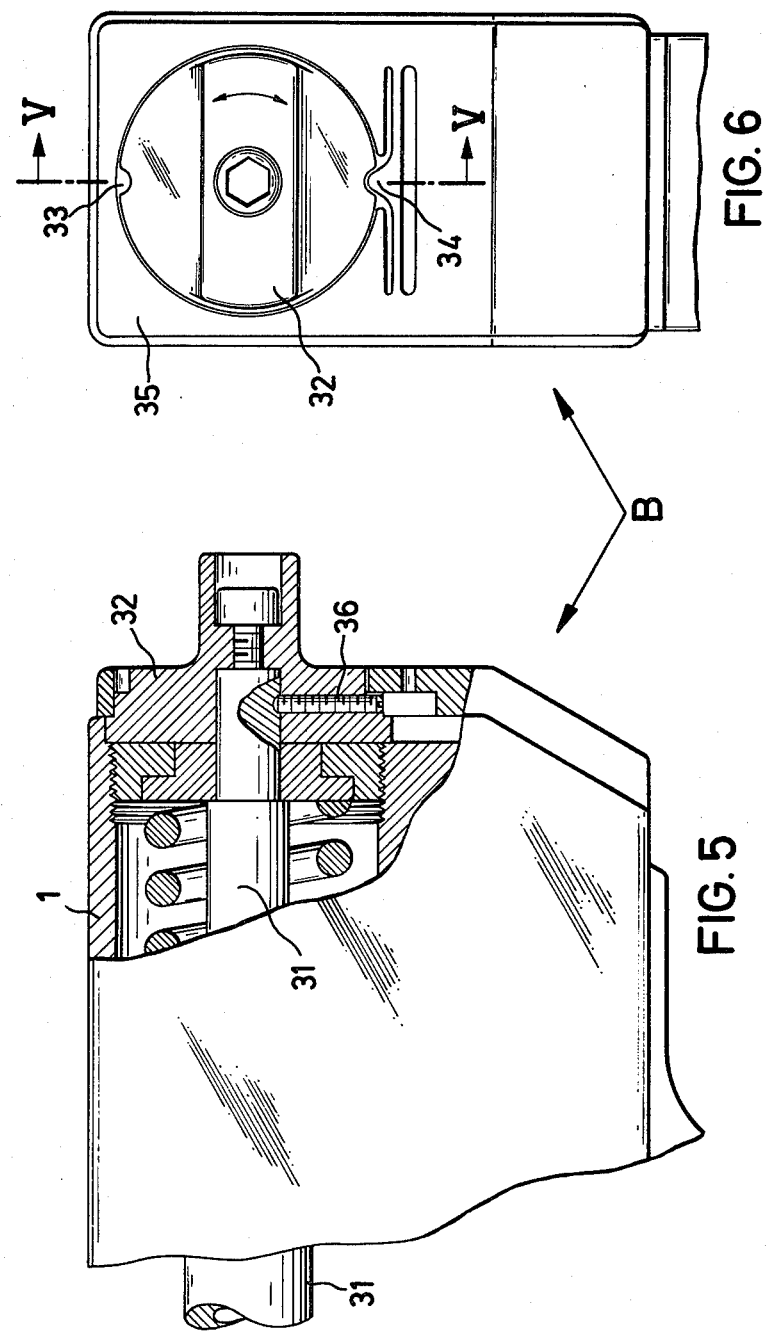

NEEDLE-LESS INJECTION INSTRUMENT

The invention relates to a needle-less injection instrument with a piston pump for the medium to be injected and with a drive motor for the piston pump, the working piston of which is arranged displaceably in a cylindrical bore of the motor housing and has a piston shaft, the pump housing being connected releasably to the motor housing and the pump plunger of the piston pump being connected releasably to the piston shaft.

Injection instruments of the type mentioned are known from German Auslegeschrift No. 1,213,958 and German Offenlegungsschrift No. 1,922,569.

In the injection syringe according to German Auslegeschrift No. 1,213,958, the housing of the vaccine pump is accommodated in the bore of the working piston and connected by means of screwing. The vaccine-pump piston has a thread at its end and is thereby screwed into the piston shaft of the working piston. A disadvantage of this is that the vaccine piump is coupled up in two steps, namely first screwing in the pump piston and then flanging on the pump housing. Not only is this operation time-consuming, but the vaccine pump also loses its sterility. When the pump is uncoupled from the motor, the pump piston also has to be drawn out from the pump housing. However, during this time, with the vaccine bottle attached, vaccine is sucked into the pump and is then lost during uncoupling. Also, a disadvantage for the operation of the injection syringe is that there is a lack of ram play between the pump and motor.

In the vaccinating gun according to German Offenlegungsschrift No. 1,922,569, the pump piston rod is connected to the working piston by means of a plug connection. The plug connection has a coupling member which is operated by means of an actuating device extending from the coupling member to the outer side of the working-piston rod. The housing of the pump is connected to the housing of the working piston via a bayonet closure. A disadvantage of this is that, during coupling, several manipulations have to be carried out at the same time. Another disadvantage is that the piston rod projects unprotected out from the pump housing, specifically that part which, during the shot, comes in contact with the vaccine chamber in the piston pump. The sterility of the vaccine pump is therefore not guaranteed. A further disadvantage is that there is a lack of ram play between the working piston and pump piston.

The invention is intended to remedy this. The invention, as defined in the claims, achieves the object by an arrangement, wherein (a) the pump housing has on the pump head an annular groove and a pair of flattened portions which are parallel to one another and which reach to the bottom of the annular groove;

(b) the pump plunger on the peg projecting from the pump chamber of the pump housing is provided with two equally deep annular grooves located next to one another and with two pairs of flattened portions which are each parallel to one another and which reach to the bottom of the grooves, one pair of flattened portions extending only from annular groove to annular groove and being arranged perpendicularly to the second pair of flattened portions;

(c) two pins are arranged, parallel to one another, respectively in the motor housing and in a bore in the piston shaft of the drive motor and engage into the annular groove of the pump housing and the annular grooves of the pump plunger; and (d) the pump plunger and the piston shaft are provided with devices preventing them from rotating in their housings.

The devices preventing the pump plunger and the piston shaft from rotating in their housings are advantageously arranged so that all the pins extend parallel to one another and the pair of flattened portions located on the pump head extends parallel to a pair of flattened portions on the pump plunger.

The advantages achieved by means of the invention are to be seen essentially in the fact that a ram play independent of the particular piston stroke is ensured between the working piston and the pump plunger. This ram play is important inasmuch as it results in a ram shock generating a short pressure shock which, however, decreases rapidly by a factor of 2 to 3. As a result of the short pressure shock, the shooting-in orifice required for the medium to be injected is produced, with a desired depth, on the subject to be injected. A further advantage is the synchronous coupling of the housings and of the pistons in one plane by one and the same manipulation. Parts of the pump which must remain sterile can at no time come into contact with contaminated parts of the motor or, during coupling, with the surrounding air. Inadvertent suction of injection medium into the piston pump during uncoupling is prevented.

The invention is explained in more detail below with reference to drawings which illustrate only one form of construction and in which:

FIG. 1 shows a partial cut-out of a side view of the needle-less injection instrument in the state after shooting; the piston pump is rotated by 90° relative to the motor housing;

FIG. 2 shows the section II—II of FIG. 1;

FIG. 3 shows a partial cut-out of a side view of the needle-less injection instrument in the cocked state;

FIG. 4 shows the section IV—IV of FIG. 3;

FIG. 5 shows the section V—V of FIG. 6;

FIG. 6 shows a view of the injection instrument from the rear;

Figure 8:
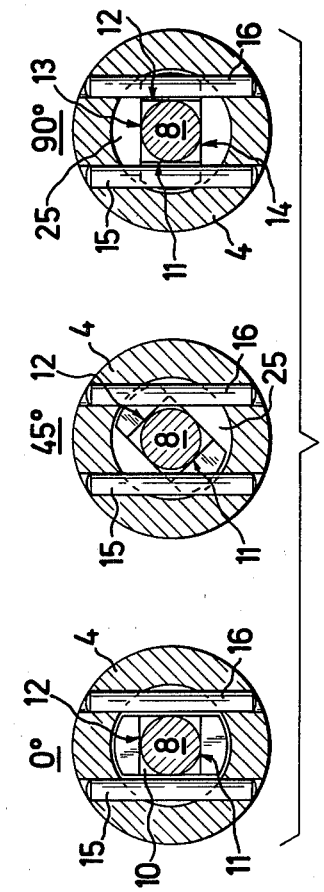
FIG. 8 shows the 1°, 45° and 90° rotation when the pump plunger is coupled to the working piston, in the sectional plane VIII—VIII of FIG. 7.

The needle-less injection instrument consists essentially of a piston pump (A) for the medium to be injected, which is connected releasably to a drive motor (B) (shown only partially). The pump housing (20) of the piston pump (A) carries a device (21) for receiving a vessel for the medium to be injected and a nozzle (26). The working piston (5) of the drive motor (B) is arranged displaceably in a cylindrical bore (6) of the motor housing (1). It has a piston shaft (4) which is guided in a bush (3). The bush (3) is located in the bore (6).

The pump housing (20) of the piston pump (A) is connected to the motor housing (1) of the drive motor (B) and the pump plunger (2) is connected to the piston shaft (4) of the working piston (5), by a coupling in each case. The couplings are designed so that the piston pump (A) and the drive motor (B) can be connected to one another or separated from one another as a result of 90° rotation in any direction. Both parts are connected securely when the piston pump is made to engage in the motor housing (1) as a result of a 90° rotation (not shown). The coupling between the pump housing (20) and the motor housing (1) is designed so that pins (27) and (28) are arranged, parallel to one another, in the motor housing (1) perpendicularly and tangentially to the cylindrical bore (6). An encircling annular groove (18) and two flattened portions (22) and (23), which are parallel to one another and which reach to the bottom of the annular groove—that is to say, the distance between the flattened portions (22) and (23) is equal to the diameter of the annular groove—are provided on the pump head (17) of the pump housing (20) in such a way that, when pushed into the cylindrical bore (19) of the bush (3), the pump head (17) fits with its flattened portions (22) and (23) between the pins (27) and (28) and, after a 90° rotation, the rear flank of the annular groove (18) comes to rest behind the pins (27) and (28)—that is to say, the distance between the pins (27) and (28) is also equal to the diameter of the annular groove (18) (FIGS. 1, 2, 3 and 4).

The coupling between the pump plunger (2) and the piston shaft (4) is, in principle, designed in the same way. The peg (8) of the pump plunger (2), which projects from the pump chamber (7) of the pump housing (20), is provided with two equally deep (of equal diameter) annular grooves (9) and (10) located next to one another and with two pairs of flattened portions (11, 12, 13 and 14) each parallel to one another. Each flattened portion reaches to the bottom of the grooves (9) and (10)—that is to say, the distance between two flattened portions (11) and (12) or (13) and (14) is equal to the diameter of the annular grooves (9) and (10).

Figure 9:
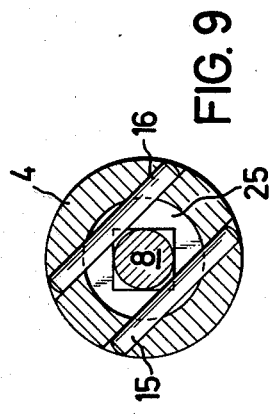
FIG. 9 shows the possibility of 90° rotation of the pump plunger, in the sectional plane IX—IX of FIG. 7.
Figure 7:
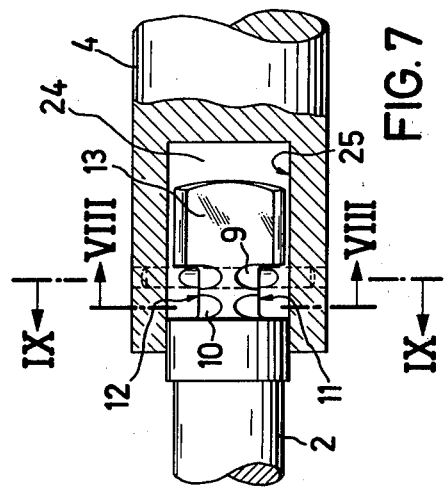
FIG. 7 shows the peg of the pump plunger with the piston shaft.

The two pairs of flattened portions are preferably perpendicular to one another. Whereas the flattened portions (13) and (14) extend from the bottom of the annular groove (10) up to the end of the pump plunger (2), the flattened portions (11) and (12) merely reach from the bottom of the annular groove (9) to the bottom of the annular groove (10). Two pins (15) and (16) are arranged, parallel to one another, in an axial bore (25) in the piston shaft (4) perpendicularly to the bore. The distance between them corresponds approximately to the inside diameter of the annular grooves (9) and (10) or to the distance between the flattened portions (11) and (12) or (13) and (14). FIGS. 7, 8 and 9 show the peg (8) of the pump plunger pushed into the bore (25) of the piston shaft (4), in the case of rotation of the pump plunger (2) through 0°, 45° and 90°. In FIG. 2, the pump head (17) is pushed into the bush (3) and the peg (8) of the pump plunger (2) is pushed into the bore (25) of the piston shaft (4). The respective flattened portions (22, 23, 11, 12, 13 and 14) are parallel to the associated pins (27, 28, 15 and 16). In FIG. 3, the piston pump (A) is rotated by 90° relative to the position according to FIG. 1 and the working motor is cocked. During cocking of the injection instrument, the pins (15) and (16) slide from the annular groove (10) (FIGS. 4 and 7) along the flattened portions (11) and (12), without touching these, into the annular groove (9), on the flank of which the pins are caught; the piston plunger is carried with them; the ram play (24) is obtained. This ram play does not change when the working stroke (dosage volume) of the piston pump is changed; its travel corresponds to the distance between the two annular grooves (9) and (10). The unloading of the injection instrument and the uncoupling of the piston pump take place correspondingly. In this case, it is appropriate always to uncouple the piston pump (A) from and couple it to the drive motor (B) with the injection instrument unloaded. It is necessary for the coupling operation that the pump plunger and the piston shaft should be secured against rotation in their housings. Such securing devices can consist of a slot (29) in the pump plunger (2) and a securing pin (30) sliding therein. Correspondingly, the pump shaft (4) can also be secured (not shown) in the bush (3). FIGS. 5 and 6 show another way of securing the piston shaft against rotation. The piston shaft (4) is connected to a rotary knob (32) via the working piston (5) and the piston rod (31). The rotary knob (32) serves for adjusting the stroke of the working piston and consequently for adjusting the dosage volume of the medium to be injected (not shown). The rotary knob (32) can have, on its periphery, grooves (33) into which engages a spring (34) located in the rear wall (35) of the motor housing (1). The grooves (33) and spring (34) are appropriately coordinated with one another so that the pins (15) and (16) of the piston shaft extend parallel to the pins (27) and (28) of the motor housing. Of course, in this case, the flattened portions (13) and (14) of the pump plunger (12) must be aligned parallel to the flattened portions (22) and (23) of the pump head. The rotary knob (32) is connected to the piston rod (31) by means of the screw (36).

We claim:

1. A needle-less injection instrument with a piston pump for the medium to be injected and with a drive motor for the piston pump, the working piston of which is arranged displaceably in a cylindrical bore of the motor housing and has a piston shaft, the pump housing being connected releasably to the motor housing and the pump plunger of the piston pump being connected releasably to the piston shaft, wherein
   (a) the pump housing (20) has on the pump head (17) an annular groove (18) and a pair of flattened portions (22, 23) which are parallel to one another and which reach to the bottom of the annular groove (18);
   (b) the pump plunger (2) on the peg (8) projecting from the pump chamber (7) of the pump housing (20) is provided with two equally deep annular grooves (9, 10) located next to one another and with two pairs of flattened portions (11, 12, 13, 14) which are each parallel to one another and which reach to the bottom of the annular grooves (9, 10), one pair of flattened portions (11, 12 or 13, 14) extending only from the annular groove (9) to the annular groove (10) and being arranged perpendicularly to the second pair of flattened portions;
   (c) two pins (15, 16, 27, 28) are arranged, parallel to one another, respectively in the motor housing (1) and in a bore (19) in the piston shaft (4) and engage into the annular groove (18) of the pump housing (20) and the annular grooves (9) and (10) of the pump plunger (2); and
   (d) the pump plunger (2) and the piston shaft (4) are provided with devices preventing them from rotating in their housings.

2. The needle-less injection instrument as claimed in claim 1, wherein the devices preventing the pump plunger (2) and the piston shaft (4) from rotating in their housings are arranged so that all the pins (15, 16, 27, 28) extend parallel to one another and the pair of flattened portions (22, 23) located on the pump head (17) extends parallel to a pair of flattened portions (15,16, 27, 28) on the pump plunger (2).

* * * * *